(12) United States Patent
Sebastian

(10) Patent No.: US 6,235,906 B1
(45) Date of Patent: May 22, 2001

(54) PREPARATION OF OPIATES

(75) Inventor: Alice Sebastian, Deptford, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 09/271,349

(22) Filed: Mar. 17, 1999

(30) Foreign Application Priority Data

Mar. 17, 1998 (GB) .................................. 9805516

(51) Int. Cl.[7] ........................ C07D 489/08; C07D 489/02
(52) U.S. Cl. ............................................ 546/45; 546/44
(58) Field of Search ..................................... 546/45

(56) References Cited

U.S. PATENT DOCUMENTS

| | | | |
|---|---|---|---|
| 2,654,756 | 10/1953 | Homeyer et al. | 260/285 |
| 4,277,604 | 7/1981 | Dauben et al. | 546/44 |

FOREIGN PATENT DOCUMENTS 408 870   1/1925   (DE) .

OTHER PUBLICATIONS

Seki, Chemical and Pharmaceutical Bulletin, vol. 18, No. 4, Jan. 1, 1970, pp. 671–676 (XP002078242).
Knorr, Chem. Ber., vol. 36, (1903), p. 3070.

Primary Examiner—Alan L. Rotman

(74) Attorney, Agent, or Firm—Pillsbury Winthrop LLP

(57) ABSTRACT

A novel process for the preparation of codeinone and analogues thereof comprising the oxidation of a compound of formula,

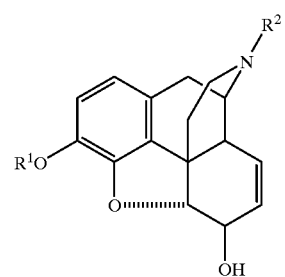

(II)

or a salt thereof, wherein $R^1$ is lower alkyl or a group

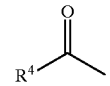

wherein $R^4$ is lower alkyl, lower alkyl substituted by halogen or phenyl, phenyl or substituted phenyl; and $R^2$ is lower alkyl, allyl or lower alkyl substituted by cycloalkyl, characterized in that the oxidation is carried out in an acidic environment is disclosed.

9 Claims, No Drawings

PREPARATION OF OPIATES

The present invention relates to a novel process for the preparation of codeinone and analogues thereof.

Codeinone is a key intermediate for the synthesis of many morphinoid compounds. It is therefore desirable for a simple, straightforward and cost effective process for its preparation.

In earlier works, codeinone was obtained from thebaine by treating it with dry HBr in $CH_2Cl_2$ at −25°, followed by hydrolysis with water and dehydrobrominating with cold NaOH (Vesely, Z., Hodkova, J. and Trojanek J., Cesk. Farm. 1986, 35, 222–6). In another method, thebaine was converted to a mixture of codeinone and neopinone in aqueous $HCO_2H$ containing $Hg(OAc)_2$ (U.S. Pat. No. 4,277,604). However, thebaine is very expensive and does not occur naturally in a high yield; therefore the preparation of codeinone from thebaine is not an attractive method.

An alternative process for the preparation of codeinone is the direct oxidation of codeine using variety of reagents, such as silver carbonate (Rapoport, H. and Reist, N. H., J. Am. Chem. Soc. 1955, 77, 490–491) and Jones' reagent (Findlay, J. W. A., Butz, R. F. and Jones, E. C., Clin. Chem. 1981, 27, 1524–1535); however, these reagents only gave codeinone in poor yield. Only Oppenauer oxidation (U.S. Pat. No. 2,654,756) has given codeinone in reasonably good yield and high purity. All these methods have their drawbacks, however. Oxidation with silver carbonate is not preferred due to its cost and incomplete reaction, whereas in the case of Jones' oxidation and Oppenauer oxidation the isolation of the product is difficult and complex.

The direct oxidation of codeine with active manganese dioxide (Ninan, A. and Sainsbury, M., Tetrahedron, 1992, 48, 6709) and γ-manganese dioxide (Highet, R. J. and Wildman, W. C., J. Am. Chem. Soc., 1955, 77, 4399) has also been reported. However, in both cases pure codeinone was obtained in only low yield due to the formation of 14β-hydroxycodeinone and low conversion.

The object of the present invention is to provide a simple process for the preparation of codeinone and analogues thereof, and which provides the desired product in high yield and purity. The present inventors have found that if oxidation of codeine or a salt thereof, for example the phosphate salt, is carried out at acidic pH, a high yield of codeinone is obtained which is not obtainable by any of the methods heretofore disclosed.

Accordingly, the present invention provides a novel process for the preparation of a compound of formula (I)

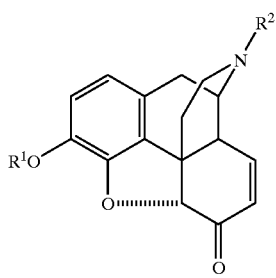

(I)

wherein $R^1$ is lower alkyl or a group

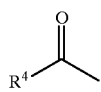

wherein $R^4$ is lower alkyl, lower alkyl substituted by halogen or phenyl, phenyl or substituted phenyl; and $R^2$ is lower alkyl, allyl or lower alkyl substituted by cycloalkyl;

comprising the oxidation of a compound of formula (II),

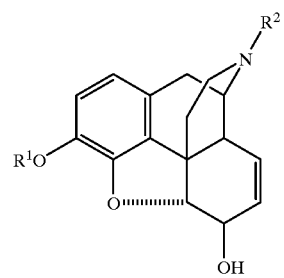

(II)

or a salt thereof, wherein $R^1$ and $R^2$ are as hereinbefore defined; characterised in that the oxidation is carried out in an acidic environment.

Preferably, each of $R^1$ and $R^2$ may be the same or different and each is lower alkyl, for example $C_{1-6}$ alkyl, such as $C_{1-4}$ alkyl, for example methyl or ethyl and preferably ethyl.

When the compound of formula (II) is present as a salt, preferably the salt is the phosphate salt ($H_3PO_4$).

Suitably the oxidation is carried out at a pH of from 0.1<pH>7; preferably, the oxidation is carried out at a pH of from 0.8<pH>4.5; most preferably the oxidation is carried out at a pH of from 0.8 to 1.2.

The solvent may be any solvent suitable for use in such an oxidation reaction. Acetone was found to be the most suitable solvent for giving the desired product in high yield and high purity. Other solvents were also found to be particularly useful and were preferred in the order: acetone>THF>IPA>$CH_3CN$>NMP. Preferably, the solvent is used as a 50:50 (v/v) solvent/water mixture.

The oxidation reagent is suitably manganese dioxide, such as activated manganese dioxide or γ-manganese dioxide, preferably γ-manganese dioxide. Suitably, the oxidation reagent is present in an amount of at least 3 equivalents or more with respect to the compound of formula (I).

The invention will now be further described by way of example only.

General Procedure for the Preparation of Codeinone from Codeine Phosphate or Codeine A solution of codeine or codeine phosphate was dissolved in the appropriate solvent system and a specified volume of hydrochloric acid of varying concentration was added. Manganese dioxide (either freshly prepared γ-manganese dioxide or activated manganese dioxide from Aldrich) was added and the reaction mixture was stirred at ambient temperature for 1.5 to 4 hours. The progress of the reaction was monitored by HPLC. The reaction mixture was filtered through a celite pad, washed with additional solvent or water, and neutralised with ammonium hydroxide. The product was extracted with methylene chloride (3×150 ml) and the combined extracts washed with water and dried over anhydrous sodium sulphate. The organic layer was then evaporated to yield codeinone.

In all the experiments the reaction was followed by HPLC and the retention time of the product was compared with that of the standard. In some cases the crude product was quantitated to obtain the purity. The HPLC analysis was done on a Shimadzu system. The column used was Phenomenex's Prodigy 5μ ODS (3) 100° A, 250×4.6 mm. The method was isocratic. The mobile phase was: water (1450 ml)+acetonitrile (550 ml)+$Et_3N$ (2 ml)+1.73 g of 1-octanesulphonate, sodium salt+pH 3.5 (adjusted with 85% phosphoric acid). In the cases where the product was isolated, it was also characterised by comparing its $^1H$ NMR with that of the standard: $^1H$ NMR ($CDCl_3$) δ1.85–1.92(1H, m, $15_\alpha$), 2.05–2.15(1H, m, $16_\alpha$), 2.27–2.4(2H, m, $15_\beta$, $10_\alpha$), 2.45(3H, s, N—CH$_3$), 2.58–2.62(1H, m, H$_{16\beta}$), 3.07–3.14 (1H, d, H$_{10\beta}$), 3.19–3.21(1H, d, H$_{9\alpha}$), 3.39–3.44(1H, m, H$_{14}$), 3.84(3H, s, OCH$_3$), 4.70(1H, s, H$_{5\beta}$), 6.05–6.11(1H, dd, H$_8$), 6.59–6.70(3H, m, H$_1$, H$_2$, H$_7$).

The following examples were carried out using the starting material and reagents indicated.

| Example No | Starting Material (g) | Solvent System (ml) | Acid (ml) | Oxidant (g) | pH | Yield (%) | Purity (HPLC area %) |
|---|---|---|---|---|---|---|---|
| 1 | Codeine (0.5) | IPA (14) H$_2$O (14) | 6N HCl (0.5) | γ-MnO$_2$ (1.6) | 1.62 | 94 | ~95 |
| 2 | Codeine phosphate (1) | IPA (22) H$_2$O (22) | — | γ-MnO$_2$ (3.2) | 4.5 | NA | ~34 |
| 3 | Codeine phosphate (0.5) | IPA (14) H$_2$O (14) | 6N HCl (0.5) | γ-MnO$_2$ (1.6) | 1.6 | 80 | 91.8 |
| 4 | Codeine (2) | IPA (40) H$_2$O (40) | 6N HCl (2) | γ-MnO$_2$ (4) | 1.44 | NA | 60.3 |
| 5 | Codeine (2) | IPA (40) H$_2$O (40) | 6N HCl (3) | γ-MnO$_2$ (7) | 1.3 | 86 | ~91.8 |
| 6 | Codeine (0.5) | IPA (10) H$_2$O (10) | 6N HCl (2) | γ-MnO$_2$ (1.5) | 0.73 | 75 | 82 |
| 7 | Codeine (0.5) | IPA (10) H$_2$O (10) | 6N HCl (1) | γ-MnO$_2$ (1.5) | 1.16 | 92 | ~97 |
| 8 | Codeine (0.5) | IPA (10) H$_2$O (10) | 6N HCl (0.75) | γ-MnO$_2$ (1.5) | 1.41 | 95 | ~95 |
| 9 | Codeine (0.5) | CH$_3$CN (10) H$_2$O (10) | 6N HCl (0.75) | γ-MnO$_2$ (1.5) | 0.9 | 89.7 | ~93 |
| 10 | Codeine (0.5) | IPA (10) H$_2$O (10) | 6N HCl (4) | γ-MnO$_2$ (1.5) | <0.1 | 50.4 | ~71 |
| 11 | Codeine (0.5) | Acetone (10) H$_2$O (10) | 6N HCl (0.75) | γ-MnO$_2$ (1.5) | 0.92 | 95.2 | 94 |
| 12 | Codeine (0.5) | THF (10) H$_2$O (10) | 6N HCl (0.75) | γ-MnO$_2$ (1.5) | 1.21 | 89 | 93 |
| 13 | Codeine (0.5) | NMP (20) | — | γ-MnO$_2$ | — | NA | ~21.6 |
| 14 | Codeine (0.5) | NMP (10) H$_2$O (10) | 6N HCl (1) | γ-MnO$_2$ | 1.45 | NA | ~90 |
| 15 | Codeine (11.45) | Acetone (200) H$_2$O (200) | 6N HCl (16) | γ-MnO$_2$ (36) | 1.02 | 83.5 | 95.5 |
| 16 | Codeine (0.5) | Acetone (10) H$_2$O (10) | 6N HCl (0.75) | Activated 85% MnO$_2$ (Aldrich) | 0.87 | NA | ~45 |
| 17 | Codeine (1) | IPA (25) CH$_2$Cl$_2$ (25) | — | γ-MnO$_2$ (3) | — | NA | ~41 |

NA = Not Available (the product was not isolated)

Preparation of γ-Manganese Dioxide

Manganese (II) sulphate monohydrate (140 g) was dissolved in 2.66 liters of water and heated to 60° C. Potassium permanganate (97.3 g) in 1.85 liter of water was added over a period of 15 minutes and stirred at 60° C. for 1 hour, until manganese dioxide precipitated out. The reaction mixture was filtered and the residue was washed with deionised water until no sulphate ion was present. The solid was dried under suction for 2 hours followed by drying at 70° C. under vacuum to a constant weight (~8 days) to give 115 g of a dark brown powder.

What is claimed is:

1. A process for the preparation of a compound of formula (I)

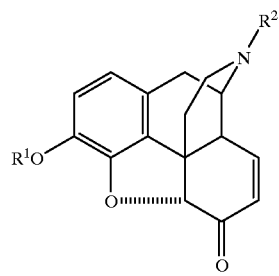

(I)

wherein R$^1$ is lower alkyl or a group

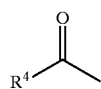

wherein R⁴ is lower alkyl, lower alkyl substituted by halogen, or phenyl or substituted phenyl; and
R² is lower alkyl, allyl or lower alkyl substituted by cycloalkyl;
comprising the oxidation of a compound of formula (II),

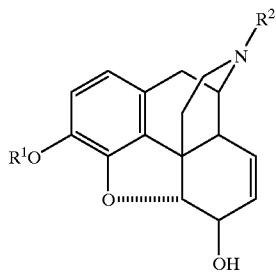

(II)

or a salt thereof, wherein $R^1$ and $R_2$ are as hereinbefore defined, and wherein the oxidation is carried out in an acidic environment and the oxidation reagent is manganese dioxide.

2. A process according to claim 1 wherein each of $R^1$ and $R^2$ are the same or different and each is lower alkyl.

3. A process according to claim 2 wherein each of $R^1$ and $R^2$ are the same or different and is methyl or ethyl.

4. A process according to claim 3 wherein $R^1$ and $R^2$ are both ethyl.

5. A process according to claim 1 wherein when the compound of formula (II) is present as a salt, the salt is the phosphate salt.

6. A process according to claim 1 wherein the oxidation is carried out at a pH of between 0.1 and 7.

7. A process according to claim 6 wherein the oxidation is carried out at a pH of between 0.8 and 4.5.

8. A process according to claim 7 wherein the oxidation is carried out at a pH of from 0.8 to 1.2.

9. A process according to claim 3, wherein R1 and R2 are both methyl.

* * * * *